United States Patent
Perriello et al.

(10) Patent No.: US 9,561,027 B2
(45) Date of Patent: *Feb. 7, 2017

(54) TISSUE GRAFT ANCHORING

(71) Applicant: Smith & Nephew, Inc., Memphis, TN (US)

(72) Inventors: Michael James Perriello, Hopedale, MA (US); Alfred Rodrigue Berube, North Attleboro, MA (US); Michael Charles Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/589,227

(22) Filed: Jan. 5, 2015

(65) Prior Publication Data

US 2015/0112385 A1    Apr. 23, 2015

Related U.S. Application Data

(63) Continuation of application No. 13/363,575, filed on Feb. 1, 2012, now Pat. No. 8,926,662.

(51) Int. Cl.
*A61B 17/04*    (2006.01)
*A61F 2/08*    (2006.01)

(52) U.S. Cl.
CPC ......... *A61B 17/0401* (2013.01); *A61F 2/0811* (2013.01); *A61B 2017/0404* (2013.01);
(Continued)

(58) Field of Classification Search
CPC ............ A61B 17/0401; A61B 17/0487; A61B 2017/0414; A61B 2017/0404; A61B 2017/0458; A61B 2017/0475; A61F 2002/0852
See application file for complete search history.

(56) References Cited

U.S. PATENT DOCUMENTS 3,580,256 A    5/1971   Wilkinson et al.
4,605,414 A    8/1986   Czajka
(Continued)

FOREIGN PATENT DOCUMENTS

CN    101170966 A    4/2008
CN    201542777      8/2010
(Continued)

OTHER PUBLICATIONS

First Office Action from related Chinese Application No. 201380015986.3 issued Apr. 1, 2016.
(Continued)

*Primary Examiner* — Katherine M Shi
*Assistant Examiner* — Michael Mendoza
(74) *Attorney, Agent, or Firm* — Burns & Levinson LLP; Joseph M. Maraia

(57) ABSTRACT

A fixation device includes a member defining at least two openings, and a suture tied to the member by passing the suture through the at least two openings in the member to form two suture loops through which ends of the suture pass. The two suture loops are interconnected. A method of securing a tissue graft includes providing the fixation member, attaching the suture to a tissue graft, and adjusting the length of the suture between the fixation member and the tissue graft by pulling the suture.

10 Claims, 8 Drawing Sheets

(52) U.S. Cl.
CPC ............... *A61B 2017/0414* (2013.01); *A61B 2017/0459* (2013.01); *A61F 2002/0852* (2013.01); *A61F 2002/0882* (2013.01)

(56) References Cited

U.S. PATENT DOCUMENTS

| | | | |
|---|---|---|---|
| 4,775,380 | A | 10/1988 | Seedhom et al. |
| 5,139,520 | A | 8/1992 | Rosenberg |
| 5,217,470 | A | 6/1993 | Weston |
| 5,234,445 | A | 8/1993 | Walker et al. |
| 5,306,301 | A | 4/1994 | Graf et al. |
| 5,405,352 | A | 4/1995 | Weston |
| 5,449,367 | A | 9/1995 | Kadry |
| 5,451,203 | A | 9/1995 | Lamb |
| 5,527,341 | A | 6/1996 | Gogolewski et al. |
| 5,645,588 | A | 7/1997 | Graf et al. |
| 5,718,717 | A | 2/1998 | Bonutti |
| 5,769,894 | A * | 6/1998 | Ferragamo .................. 606/148 |
| 5,893,592 | A | 4/1999 | Schulze et al. |
| 5,989,252 | A | 11/1999 | Fumex |
| 6,143,029 | A | 11/2000 | Rippstein |
| 6,193,754 | B1 | 2/2001 | Seedhom |
| 6,203,572 | B1 | 3/2001 | Johnson et al. |
| 6,296,659 | B1 | 10/2001 | Foerster |
| 6,506,197 | B1 | 1/2003 | Rollero et al. |
| 6,517,578 | B2 | 2/2003 | Hein |
| 6,533,802 | B2 | 3/2003 | Bojarski et al. |
| 6,602,290 | B2 | 8/2003 | Esnouf et al. |
| 6,652,561 | B1 | 11/2003 | Tran et al. |
| 7,601,165 | B2 | 10/2009 | Stone |
| 7,651,509 | B2 | 1/2010 | Bojarski et al. |
| 7,658,751 | B2 | 2/2010 | Stone et al. |
| 7,749,250 | B2 | 7/2010 | Stone et al. |
| 7,905,904 | B2 | 3/2011 | Stone et al. |
| 8,137,382 | B2 | 3/2012 | Denham et al. |
| 8,439,976 | B2 | 5/2013 | Albertorio et al. |
| 8,460,379 | B2 | 6/2013 | Albertorio et al. |
| 2001/0041938 | A1 | 11/2001 | Hein |
| 2002/0029066 | A1 | 3/2002 | Foerster |
| 2002/0115999 | A1 | 8/2002 | McDevitt et al. |
| 2002/0165611 | A1 | 11/2002 | Enzerink et al. |
| 2002/0173788 | A1 | 11/2002 | Bojarski et al. |
| 2003/0050666 | A1 | 3/2003 | Grafton |
| 2004/0097943 | A1 | 5/2004 | Hart |
| 2004/0181234 | A1 | 9/2004 | McDevitt et al. |
| 2004/0220573 | A1 | 11/2004 | McDevitt et al. |
| 2005/0149118 | A1 | 7/2005 | Koyfman et al. |
| 2005/0251159 | A1 | 11/2005 | Ewers et al. |
| 2005/0251205 | A1 | 11/2005 | Ewers et al. |
| 2005/0277985 | A1 | 12/2005 | Wert et al. |
| 2006/0155328 | A1 | 7/2006 | Foerster |
| 2006/0190041 | A1 | 8/2006 | Fallin et al. |
| 2007/0010857 | A1 | 1/2007 | Sugimoto et al. |
| 2007/0016244 | A1 | 1/2007 | Behl et al. |
| 2007/0156174 | A1 | 7/2007 | Kaiser et al. |
| 2007/0162125 | A1 | 7/2007 | LeBeau et al. |
| 2007/0239209 | A1 | 10/2007 | Fallman |
| 2007/0250163 | A1 | 10/2007 | Cassani |
| 2007/0270857 | A1 | 11/2007 | Lombardo et al. |
| 2008/0027446 | A1 | 1/2008 | Stone et al. |
| 2008/0065114 | A1 | 3/2008 | Stone et al. |
| 2008/0082128 | A1 | 4/2008 | Stone |
| 2008/0177336 | A1 | 7/2008 | Cerundolo |
| 2008/0195148 | A1 | 8/2008 | Cook et al. |
| 2008/0208204 | A1 | 8/2008 | Schmieding et al. |
| 2008/0208252 | A1 | 8/2008 | Holmes |
| 2008/0228186 | A1 | 9/2008 | Gall et al. |
| 2008/0255613 | A1 | 10/2008 | Kaiser et al. |
| 2008/0312689 | A1 | 12/2008 | Denham et al. |
| 2009/0036905 | A1 | 2/2009 | Schmieding |
| 2010/0145395 | A1 | 6/2010 | Graf et al. |
| 2010/0268273 | A1 | 10/2010 | Albertorio et al. |
| 2010/0324608 | A1 | 12/2010 | Albertorio et al. |
| 2011/0238179 | A1 | 9/2011 | Laurencin et al. |
| 2011/0264141 | A1 | 10/2011 | Denham et al. |
| 2012/0123541 | A1 | 5/2012 | Albertorio et al. |
| 2013/0096612 | A1 | 4/2013 | Zajac et al. |

FOREIGN PATENT DOCUMENTS

| | | |
|---|---|---|
| EP | 0598219 A2 | 5/1994 |
| EP | 0744165 A1 | 11/1996 |
| FR | 2638349 B1 | 12/1990 |
| WO | 01/70135 A2 | 9/2001 |
| WO | 2007005394 A1 | 1/2007 |
| WO | 2009029914 A1 | 3/2009 |

OTHER PUBLICATIONS

Search Report from related Chinese Application No. 201380015986.3 issued Mar. 23, 2016.
International Search Report, PCT/US2013/024231, Jun. 10, 2013.
International Search Report and Written Opinion for International Application PCT/US2012/023056 mailed Jun. 13, 2012.
Invitation to Pay Additional Fees and Communication Relating to the Result of the Partial International Application No. PCT/US2012/023056 mailed Apr. 16, 2012.
Office Action from related European Application No. 13712976.3-1662 issued Sep. 16, 2016.
Second Office Action from related Chinese Application No. 201380007899.3 issued May 23, 2016.
Office Action from related Russian Application No. 2014133969/14(054900) issued Aug. 11, 2016.
Patent Examination Report from related Australian Application No. 2013235641 issued Nov. 10, 2016.
Office Action from related Japanese Application No. 2014-555727 issued Nov. 7, 2016.

* cited by examiner

TISSUE GRAFT ANCHORING

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

SUMMARY

To increase the graft/channel interface in femoral fixation for cruciate repair the distance between a graft fixation member and the tendon construct is reduced. The ability to minimize this distance is generally limited by fixation member flipping constraints, which results in less tendon in the femoral channel, or leads to making compromises in the size of the graft fixation member to accommodate the tendon and the flipping of the graft fixation member.

According to one aspect, a method of securing a tissue graft includes providing a fixation member having a suture tied thereto by passing the suture through at least two openings in the fixation member to form two suture loops through which ends of the suture pass, attaching the suture to the tissue graft, and adjusting the length of the suture between the fixation member and the tissue graft by pulling the suture.

Embodiments of this aspect may include one or more of the following features.

The two suture loops are interconnected. Attaching the suture includes forming a loop of soft tissue of the tissue graft over the suture. Attaching the suture includes passing the suture through a bone block of the tissue graft followed by tying the suture to the fixation member. The method includes passing the fixation member, suture, and attached tissue graft through a bone passage, followed by adjusting the length of the suture between the fixation member and the tissue graft.

According to another aspect, a fixation device includes a member defining at least two openings, and a suture tied to the member by passing the suture through the at least two openings in the member to form two suture loops through which ends of the suture pass.

Embodiments of this aspect may include one or more of the following features.

The two suture loops are interconnected. The member is elongated in a first dimension defining a length that extends between first and second ends of the member, and the member has a second dimension transverse to the first dimension that is smaller than the length. The member defines four, six, or seven holes.

The details of one or more implementations are set forth in the accompanying drawings and the description below. Other features, objects, and advantages of the disclosure will be apparent from the description and drawings, and from the claims.

DETAILED DESCRIPTION

Figure 1A:
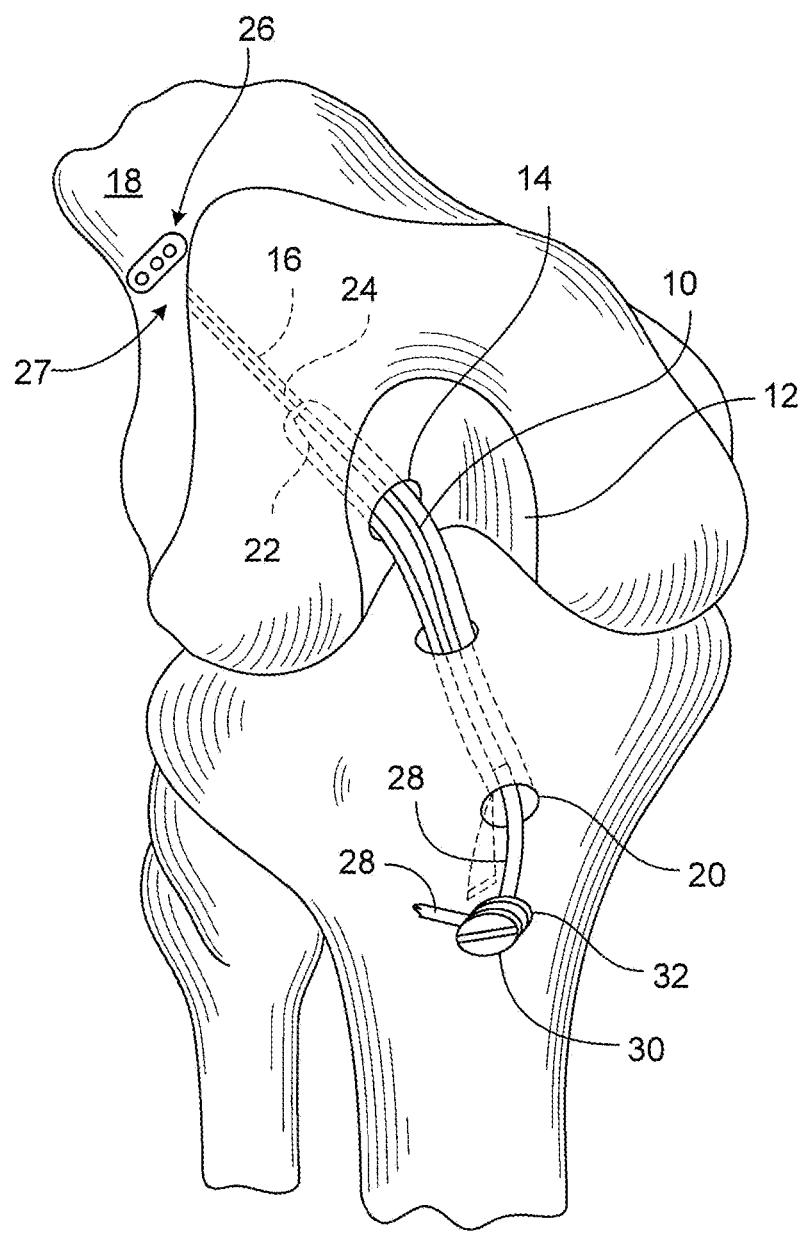
FIGS. 1A and 1B are illustrations of a tissue graft secured within the knee by a graft fixation member.
Figure 1B:
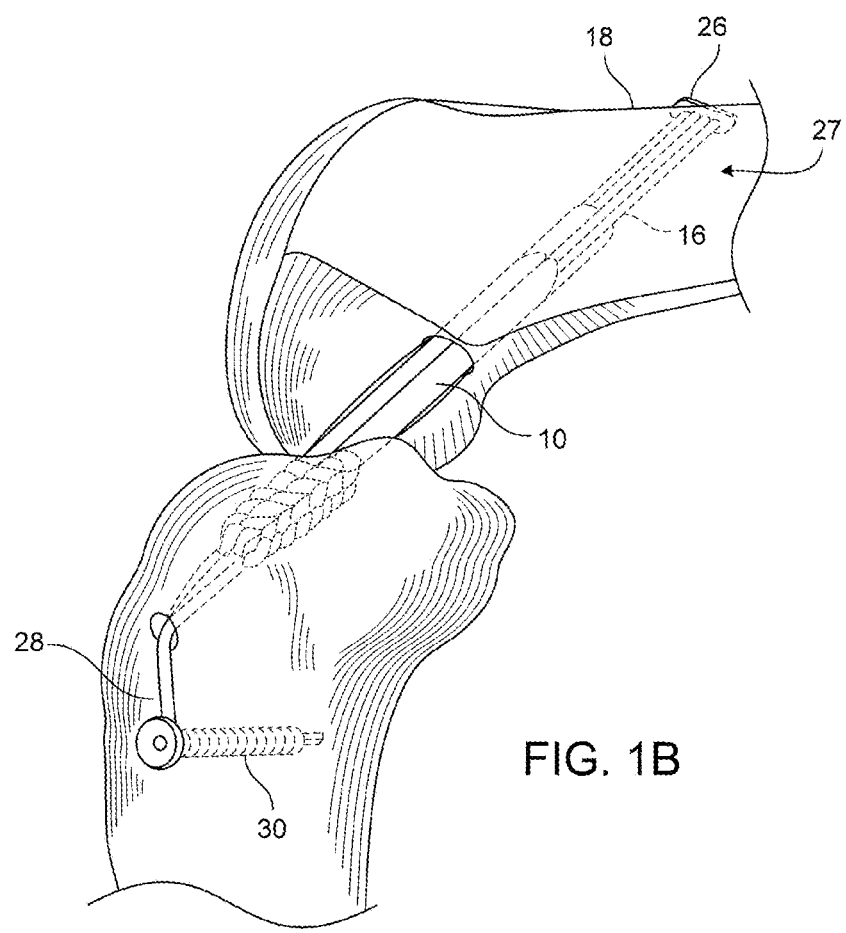

Referring to FIGS. 1A and 1B, a knee joint has a tissue graft 10 (e.g., a patellar tendon graft (FIG. 1A) or a semitendonosis and gracilis graft (FIG. 1B)) implanted in an anterior cruciate ligament (ACL) repair and reconstruction procedure. Prior to implanting tissue graft 10, a notchplasty procedure is preferably performed to expand the intercondylar notch 12 of the femur bone. A femoral channel 14 for receiving one end of tissue graft 10 is then drilled from notch 12 a predetermined distance within the femur with a passing channel 16 of reduced diameter drilled further through the femur from femoral channel 14 to a region of femoral cortex 18. A tibial channel 20 for receiving the other end of tissue graft 10 is drilled from an anterior region of the tibia to a region near the opening of femoral channel 14.

In the case of patellar tendon graft, one end of tissue graft 10 includes a bone block 22 which is shaped and sized in close conformity with femoral channel 14 to ensure optimal healing. A length of suture 24 has one end attached to bone block 22 and the other end secured at femoral cortex region 18 with a graft fixation member 26 of a fixation device 27. The suture 24 is attached to the graft fixation member 26 in a manner that permits the length of the suture 24 between the graft fixation member 26 and the tissue graft 10 to be adjusted prior to or after the graft 10 and the fixation member 26 have been positioned as shown in FIGS. 1A and 1B. The other end of tissue graft 10 includes a second length of suture 28 which is attached to the tibia, for example, with a fixation screw 30. A washer 32 either attached to or positioned under the head of fixation screw 30 helps in holding the suture in place when screw 30 is tightened.

The graft fixation member 26 is positioned using pull threads (not shown) attached to the member. The pull threads are passed through the channels 14 and 16 from the notch 12 to the cortex 18 and used to pull the graft fixation member 26 through the channels 14 and 16 with a long axis of the graft fixation member aligned with the channels. After exiting the channel 16, the pull threads are used to flip the graft fixation member 26 so that the member 26 lies flat against the cortex.

Figure 2:
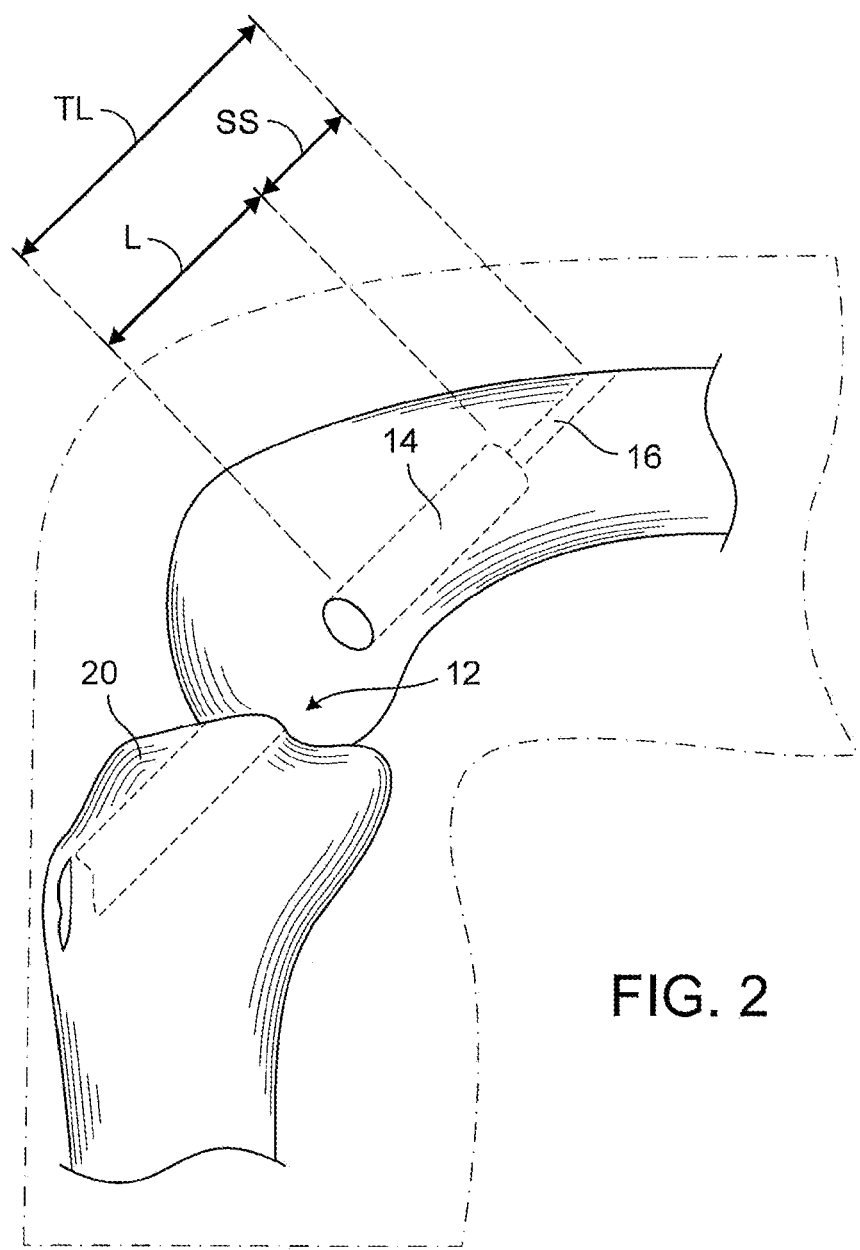
FIG. 2 is another view of the knee joint of FIG. 1.

Referring to FIG. 2, length (L) of femoral channel 14 is selected by the surgeon in accordance with the length of bone block 22 and the desired insertion distance of tissue graft 10 within the femur. The span of suture 24, designated as SS, is approximately that of passing channel 16 so that the sum of the desired insertion length (L) and span of suture (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

The ability to adjust the length of the suture 24 allows the length of the suture span (SS) to be minimized, only being limited by the desired length of passing channel 16. There is a minimum length of the suture 24 that is necessary during passage of the graft fixation member 26 through the channel 14, 16 to allow the member 26 to be positioned in alignment with the channels. Once the graft fixation member 26 is located against the femoral cortex 18, the length of the suture 24 can be shortened by pulling on the suture to maximize the amount of the tissue graft 10 that is located within the femoral channel 14.

Figure 3:
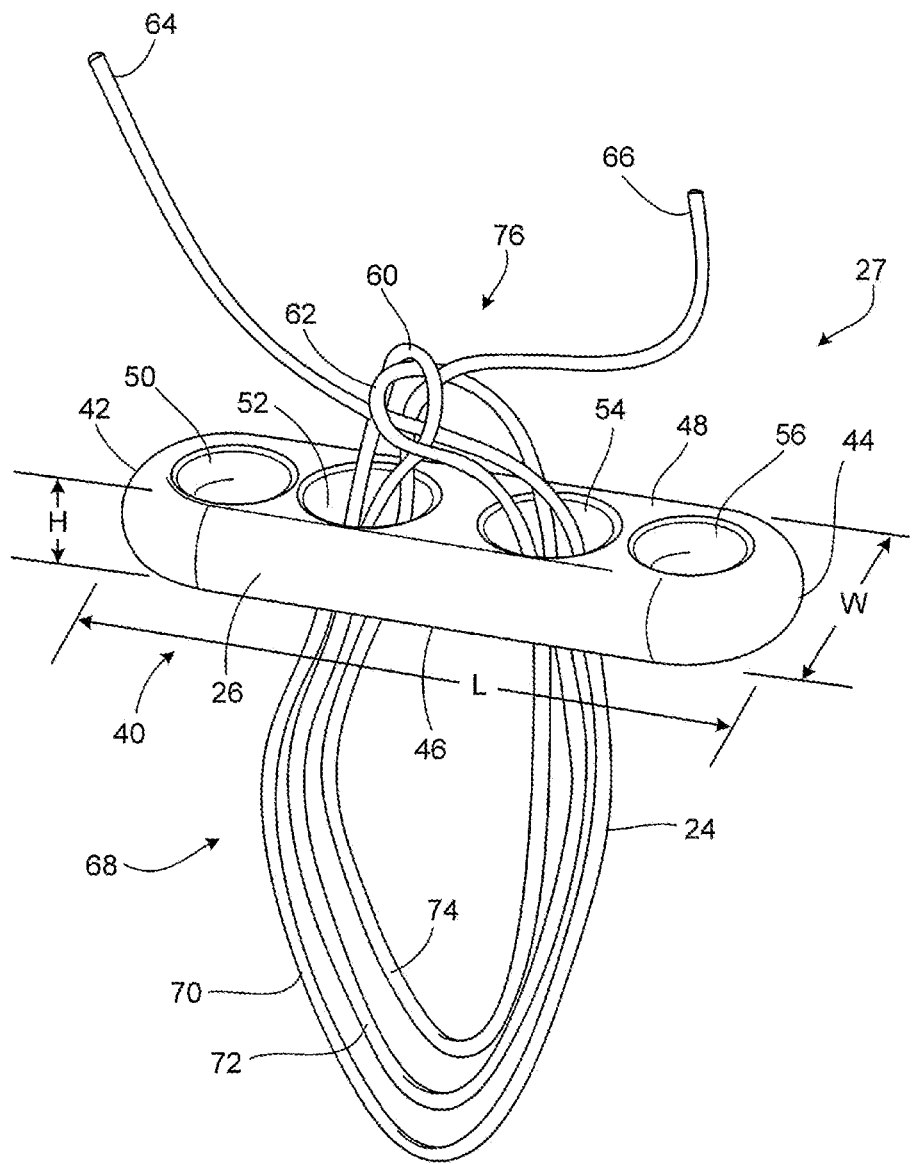
FIGS. 3-6 are perspective views of embodiments of fixation devices.

The suture 24 is a woven or braided suture, for example, #5 Ultrabraid suture, attached to the graft fixation member 26 in a loop and knot configuration to form a fixation device 40. Referring to FIG. 3, the graft fixation member 26 is elongated in a first dimension defining a length, L, that extends between a first end 42 and a second end 44 of the member 26, a second dimension transverse to the first dimension that has a width, W, smaller than the length, L, and a third dimension transverse to the first and second dimensions that has a height, H, small than the length, L. The graft fixation member has a bone contacting side 46 and an opposite side 48. Extending between the sides 46, 48 are four holes 50, 52, 54 and 56. The holes 50 and 56 receive the passing sutures, not shown.

The suture 24 is a single length of suture passed through holes 52 and 54 to form two interconnecting loops 60, 62 through which ends 64, 66, respectively, of the suture 24 are passed, created a knot 76 and a loop 68 of three suture loops 70, 72, and 74. To form the loop and knot configuration, for example, the end 66 of the suture 24 is passed down through hole 54 and up through hole 52, creating loop 70; folded over on itself, around the length of suture extending up from hole 54, and passed back down hole 52, creating loop 60; passed up through hole 54, creating loop 72; passed through loop 60, folded over on itself, and passed back down hole 54, creating loop 62 interconnected with loop 60; passed up through hole 52, creating loop 74; and then passed through loop 62.

By pulling on the ends 64, 66 of the suture 24, the length of the loop 68 can be adjusted, for example, from a minimum that equals the distance between the holes 52 and 54 to about 30 mm, such that, with the tissue graft 10 attached the suture 24, the distance between the graft fixation member 26 and the tissue graft 10 can be adjusted between 0 mm and about 15 mm.

When the fixation device 40 is used with a semitendonosis and gracilis graft (FIG. 1B), the suture 24 can be provided to the surgeon pre-tied to the graft fixation member 26, and operating room personnel attach the tissue graft to the fixation device 40 by passing the tissue graft through the suture loop 68. When a patellar tendon graft (FIG. 1A) is used, operating room personnel form the loop and knot configuration by passing the suture through the bone block of the graft while forming the loop and knot configuration.

The distance between the graft fixation member 26 and the tissue graft 10 can be adjusted while the graft/fixation member construct is in the femoral tunnel. Alternatively, the distance is determined by the surgeon prior to placing the graft.

Once the graft fixation member 26 and the tissue graft 10 are positioned in the knee with the desired length of the suture 24, tension placed on the suture by the tissue graft acts to secure the loop and knot configuration.

The length, width and height of the fixation member 26, is for example, 12 mm.times.4 mm.times.1.5 mm.

Other embodiments are within the scope of the following claims.

Figure 4:
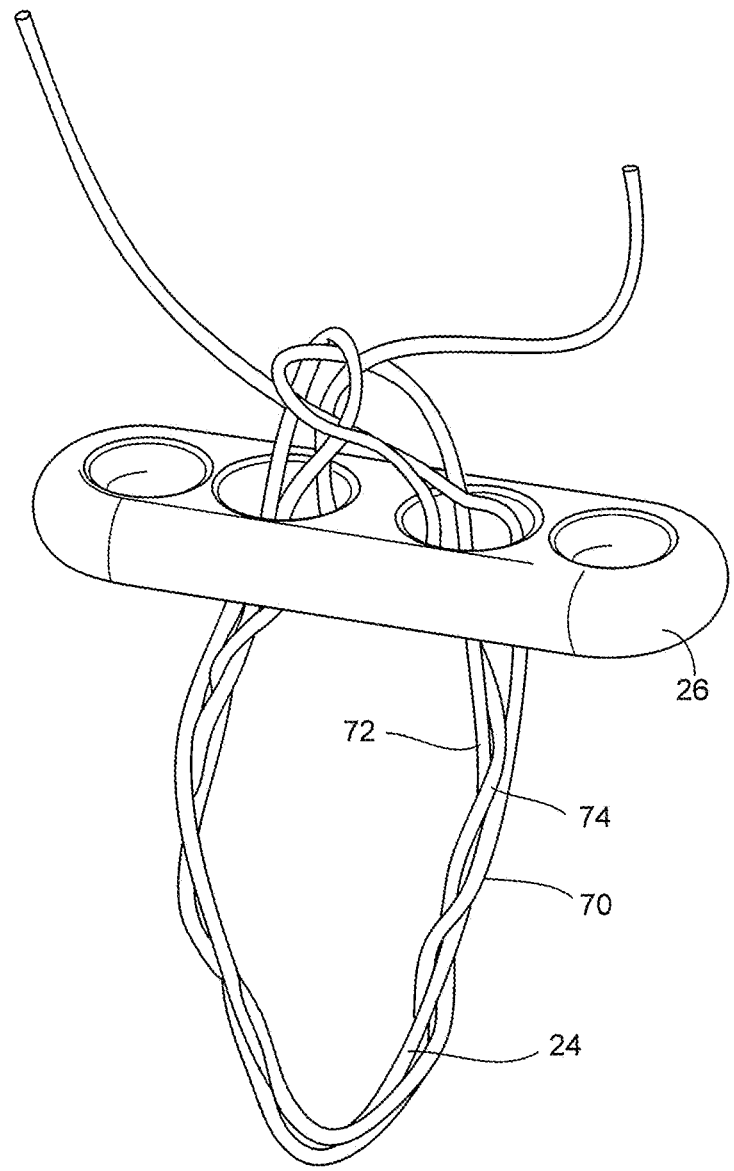
Figure 5:
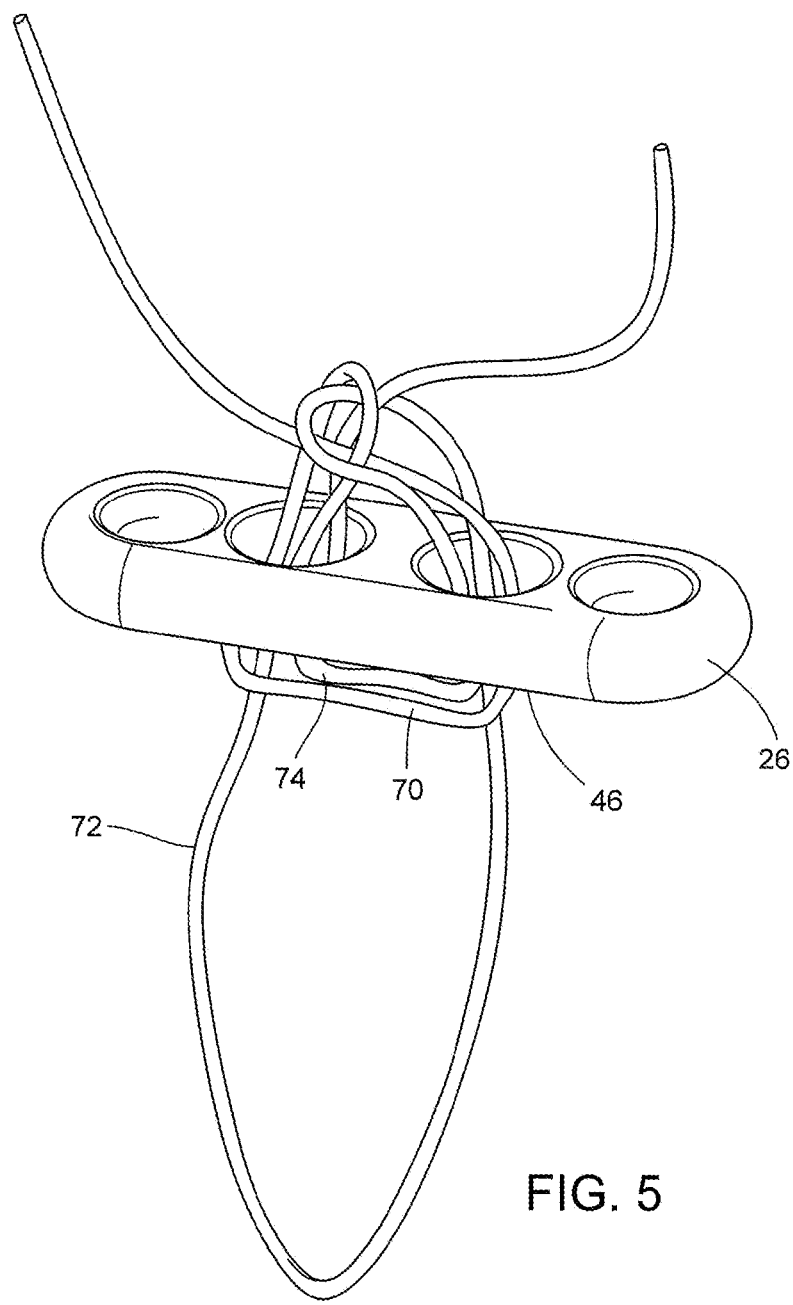
Figure 6:
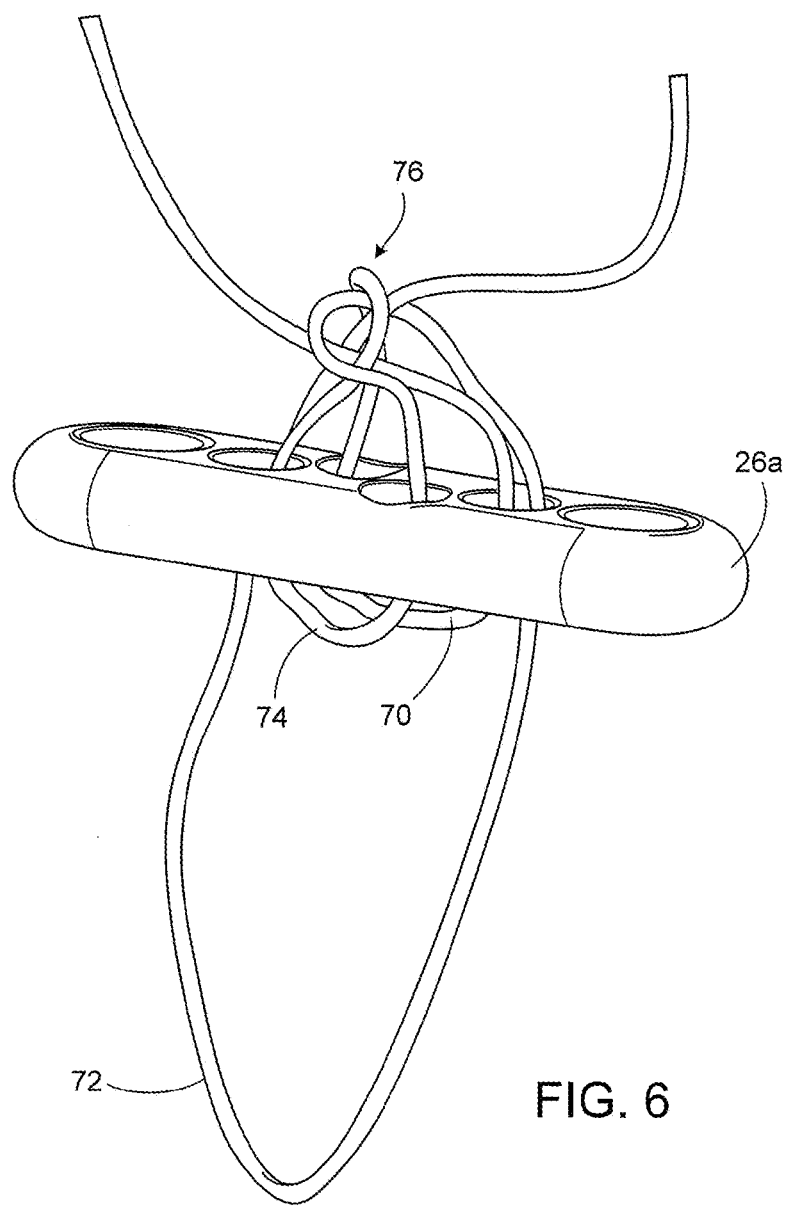
Figure 7B:
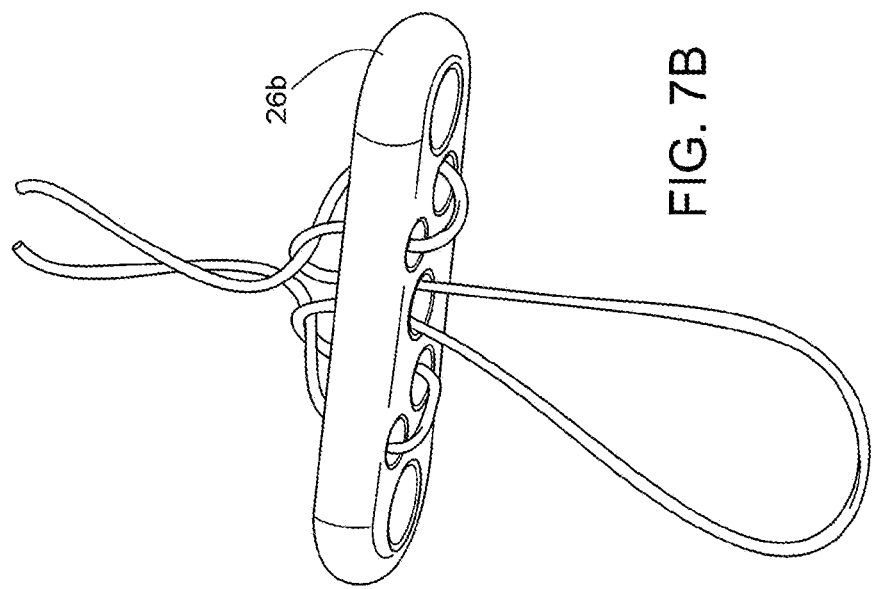
FIGS. 7A and 7B are perspective views of an additional embodiment of a fixation device.
Figure 7A:
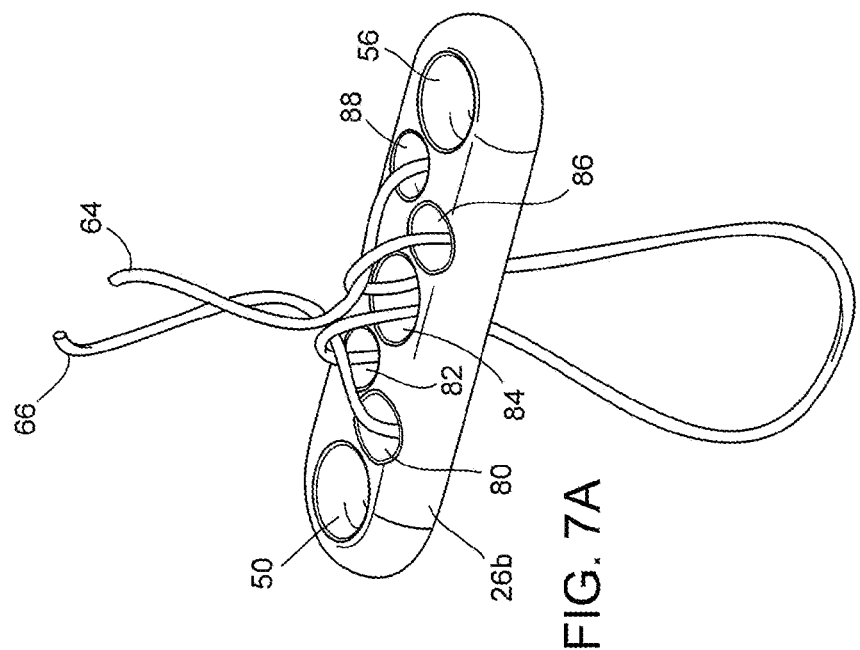

For example, referring to FIG. 4, the suture loops 70, 72 and 73 can be twisted. Referring to FIG. 5, the suture loops 70 and 74 can be tightened against the bone contacting side 46 of the graft fixation member 26 such that in use the tissue graft is only attached to loop 72. The graft fixation member 26a of FIG. 6 includes six holes with the suture 24 being passed through four central holes to form loops 70, 72 and 74, and knot 76. The graft fixation member 26b of FIGS. 7A and 7B includes seven holes with the suture 24 being passed through five central holes 80, 82, 84, 86 and 88. The form the suture construct, the suture end 66 is passed down through hole 88, up through hole 86, over the suture extending up from hole 88, down through hole 84, looped and passed back up through hole 84, down through hole 82, up through hole 80, and through the loop formed between holes 84 and 82.

The graft fixation member can be modified to aid flipping of the member by providing open or closed ends, and variation in thickness, length or width. To aid in positioning the graft fixation member at the end of the channel, the member can have a banana shape or modifications such as rectangular, triangular or other geometric shapes. To aid in strength of pull out the thickness of the graft fixation member between the holes in the member can be adjusted. This section of the graft fixation member between the holes can be modified by increasing or reducing its thickness to open the space for and reduce the distance between the graft fixation member and the tissue graft.

The graft fixation member can include only a single opening with the suture tied to graft fixation member by passing the suture through the single opening in the member to form two suture loops through which ends of the suture pass.

Other implementations are within the scope of the following claims.

What is claimed is:

1. A method of securing a tissue graft comprising:
attaching a suture of a fixation member to a tissue graft, the suture of the fixation member comprising a knot and loop configuration tied thereto by passing the suture through at least two openings in the fixation member to form two suture loops through which ends of the suture pass; creating a first suture loop; folding the suture over on itself, creating a first interconnecting loop; passing the suture up through a first opening, creating a second suture loop; passing the suture through first interconnecting loop, and folding the suture over on itself, and passing the suture back down a second opening, creating another interconnecting loop interconnected with the first interconnecting loop, passed up through the first opening; and creating third suture loop, and passing the third suture loop through the another interconnecting loop; and
adjusting the length of the suture between the fixation member and the tissue graft by pulling the suture.

2. The method of claim 1 wherein attaching the suture comprises forming a loop of soft tissue of the tissue graft over the suture.

3. The method of claim 1 wherein attaching the suture comprises passing the suture through a bone block of the tissue graft followed by tying the suture to the fixation member.

4. The method of claim 1 comprising passing the fixation member, suture, and attached tissue graft through a bone passage, followed by adjusting the length of the suture between the fixation member and the tissue graft.

5. A fixation device comprising:
a member defining at least one opening; and
a suture tied to the member by passing the suture through the at least one opening in the member to form two suture loops through which ends of the suture pass creating a first suture loop; folding the suture over on itself, creating a first interconnecting loop; passing the suture up through a first opening, creating a second suture loop; passing the suture through first interconnecting loop, and folding the suture over on itself, and passing the suture back down a second opening, creating another interconnecting loop interconnected with the first interconnecting loop, passed up through the first opening; and creating third suture loop, and passing the third suture loop through the another interconnecting loop.

6. The fixation device of claim 5 wherein the member is elongated in a first dimension defining a length that extends between first and second ends of the member, the member having a second dimension transverse to the first dimension that is smaller than the length.

7. The fixation device of claim 5 wherein the member defines two openings.

8. The fixation device of claim 5 wherein the member defines four openings.

9. The fixation device of claim 5 wherein the member defines six openings.

10. The fixation device of claim 5 wherein the member defines seven openings.

* * * * *